(12) United States Patent
Dubey et al.

(10) Patent No.: US 8,616,879 B2
(45) Date of Patent: Dec. 31, 2013

(54) CAPSULE AND DELIVERY TIP WITH TRANSITION PORTION FOR DISPENSING VISCOUS REACTIVE DENTAL MATERIALS

(75) Inventors: Ryan Dubey, Meriden, CT (US); Jay Grady, Walcott, CT (US); David Saily, Ridgefield, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 13/472,856

(22) Filed: May 16, 2012

(65) Prior Publication Data

US 2012/0258423 A1  Oct. 11, 2012

Related U.S. Application Data

(63) Continuation-in-part of application No. 13/069,161, filed on Mar. 22, 2011, and a continuation-in-part of application No. 29/413,845, filed on Feb. 21, 2012, now Pat. No. Des. 683,453, and a continuation of application No. PCT/US2012/029845, filed on Mar. 20, 2012.

(51) Int. Cl.
*A61C 17/00* (2006.01)
*A61C 17/02* (2006.01)
*A61C 5/04* (2006.01)

(52) U.S. Cl.
USPC ................................. 433/80; 433/89; 433/90

(58) Field of Classification Search
USPC .................. 433/80–82, 88–90, 215, 126; 604/833–536, 82–92, 200–203, 222, 604/206, 240–243; 285/331–332; 206/219; 222/566–568, 386–390
See application file for complete search history.

(56) References Cited

U.S. PATENT DOCUMENTS

| | | | | |
|---|---|---|---|---|
| 4,236,516 A | | 12/1980 | Nilson | 604/214 |
| 4,369,781 A | * | 1/1983 | Gilson et al. | 604/403 |
| 4,758,158 A | | 7/1988 | Pierce et al. | 433/90 |
| 4,824,145 A | * | 4/1989 | Carlsson | 285/38 |
| 5,052,927 A | | 10/1991 | Discko, Jr. | 433/90 |
| 5,125,892 A | * | 6/1992 | Drudik | 604/90 |
| 5,289,919 A | | 3/1994 | Fischer | 206/571 |
| 5,336,088 A | | 8/1994 | Discko, Jr. | 433/90 |
| 5,362,495 A | * | 11/1994 | Lesage | 424/435 |
| D353,673 S | | 12/1994 | Discko, Jr. et al. | D24/152 |
| 5,413,564 A | | 5/1995 | Silver et al. | 604/323 |
| D359,119 S | | 6/1995 | Dragan et al. | D24/114 |
| 5,489,207 A | | 2/1996 | Dragan et al. | 433/90 |
| 5,573,281 A | * | 11/1996 | Keller | 285/40 |
| 5,616,136 A | * | 4/1997 | Shillington et al. | 604/240 |
| 5,637,101 A | * | 6/1997 | Shillington | 604/242 |
| 5,743,886 A | * | 4/1998 | Lynn et al. | 604/191 |
| 5,860,806 A | | 1/1999 | Prantisis et al. | 433/80 |
| 5,876,384 A | | 3/1999 | Dragan et al. | 604/264 |
| 6,135,771 A | * | 10/2000 | Dragan et al. | 433/90 |

(Continued)

*Primary Examiner* — Yogesh Patel
(74) *Attorney, Agent, or Firm* — Fattibene and Fattibene LLC; Paul A. Fattibene

(57) ABSTRACT

A material capsule containing a reactive or caustic dental material and a separately attachable delivery tip having a metal cannula. A material capsule for placement in a syringe contains a reactive or caustic dental material for dispensing through a metal cannula. The material capsule is sealed for storing the caustic or reactive dental material, preventing prolonged contact with or proximity to the metal cannula of a delivery tip. Contact with the reactive or caustic dental material only occurs during actual dispensing. Transition portions facilitate dispensing of viscous material. External grips facilitate attachment of the delivery tip. The dispensing and accurate placement of caustic or reactive dental materials is facilitated, making dentistry easier.

6 Claims, 8 Drawing Sheets

(56) References Cited

U.S. PATENT DOCUMENTS

| | | |
|---|---|---|
| D435,292 S | 12/2000 | Dragan et al. ............... D24/152 |
| 6,261,094 B1 | 7/2001 | Dragan ........................... 466/90 |
| 6,302,574 B1 | 10/2001 | Chan ........................ 366/160.4 |
| 6,328,715 B1 | 12/2001 | Dragan et al. ................ 604/232 |
| D460,822 S | 7/2002 | Dragan et al. ............... D24/152 |
| 6,626,870 B1 * | 9/2003 | Yarborough et al. ......... 604/199 |
| 6,682,348 B2 | 1/2004 | Lawter et al. .................. 433/90 |
| 7,748,567 B2 | 7/2010 | Horner et al. ................. 222/135 |
| 7,942,669 B2 | 5/2011 | Dragan et al. ................ 433/136 |
| 8,123,727 B2 * | 2/2012 | Luther et al. ................. 604/249 |
| 2002/0010430 A1 | 1/2002 | Dragan et al. ................ 604/217 |
| 2003/0146116 A1 | 8/2003 | Klein et al. |
| 2004/0152041 A1 | 8/2004 | Metzbower ..................... 433/90 |
| 2005/0008583 A1 | 1/2005 | White ............................. 424/49 |
| 2006/0271015 A1 * | 11/2006 | Mantell ......................... 604/533 |
| 2007/0148623 A1 | 6/2007 | Dias et al. .................... 433/223 |
| 2007/0164047 A1 | 7/2007 | Reidt et al. .................... 222/137 |
| 2009/0061393 A1 | 3/2009 | Kollefrath et al. ............ 433/226 |
| 2009/0289084 A1 * | 11/2009 | Kunishi et al. ............... 222/386 |
| 2010/0174268 A1 | 7/2010 | Wilmot et al. ................ 604/506 |
| 2010/0240004 A1 | 9/2010 | Zalsman ......................... 433/90 |
| 2010/0255443 A1 | 10/2010 | Dragan ......................... 433/136 |

* cited by examiner

CAPSULE AND DELIVERY TIP WITH TRANSITION PORTION FOR DISPENSING VISCOUS REACTIVE DENTAL MATERIALS

RELATED APPLICATIONS

This application is a continuation-in-part of application Ser. No. 13/069,161 filed Mar. 22, 2011; a continuation-in-part of application Ser. No. 29/413,845 filed Feb. 21, 2012; and a continuation of International Application No. PCT/US2012/29845 filed Mar. 20, 2012.

FIELD OF THE INVENTION

The present invention relates in general to the dispensing of a dental material, and more particularly to the delivery of a dental material that may react with metal.

BACKGROUND OF THE INVENTION

In practicing dentistry it is often necessary to precisely position small quantities of material in difficult to reach locations within a patient's mouth. Some of these materials are often difficult to work with because Accordingly there have been many devices developed to aid the dentist or dental practitioner in the placement of different dental materials. One such invention is disclosed in U.S. Pat. No. 5,489,207 entitled "Dental Cartridge Extruder with Rigid Drop in Front End", issuing to Dragan et al on Feb. 6, 1996. Therein disclosed is a manual dental extruder or syringe used in combination with a dental cartridge, capsule, or ampoule for extruding viscous dental material, which is herein incorporated by reference.

Additionally in dentistry various capsules or tips have been developed for specific applications. One such capsule is disclosed in U.S. Pat. No. 5,052,927 entitled "Syringe and Disposable Capsule with Cannula for Use Therewith" issuing to Discko, Jr., on Oct. 1, 1991. Therein disclosed is a capsule for dispensing a dental material having a metal cannula thereon permitting precise placement of the dental material.

Another application for a tip is disclosed in U.S. Pat. No. 5,876,384 entitled "Micro Aspirator" issuing to Dragan et al on Mar. 2, 1999. Therein disclosed is an aspirating tip placed on a flexible tube for removing blood, debris and fluids from around a small surgical site.

Another dental cartridge intended for a specific application is disclosed in U.S. Pat. No. 6,135,771 entitled "Dental Cartridge Having an Attachable Delivery Portion" issuing to Dragan et al on Oct. 24, 2000. Therein disclosed is a dental cartridge or capsule having a body portion and a delivery portion or a cap with a metal cannula. The dental cartridge permits the mixing of a first component, typically a powder, and a liquid component of dental material prior to dispensing.

While these prior dental devices have made dentistry easier for the practicing dentist in their particular or specific areas of application, there is a continuing need to develop specialized delivery systems for specific dental materials so as to make dentistry easier. The reactivity or caustic nature of some dental materials to metal has created problems in storing these dental materials in a unit dose capsule designed for precise placement with a metal cannula. Some dental materials, such as material containing chemicals that may react with metal, have been difficult to store and dispense. For example, aluminum chloride may be used as a component in a dental material. Aluminum chloride will react with metal if maintained in contact or in close proximity with the metal for a relatively long time. There have been continuing problems using a unit dose container having a metal cannula containing a dental material that may react with the metal cannula. As a result, the dental material may become unusable or may cause undesirable effects such as discoloration or a failure to perform as desired. Therefore, there is a need for a specialized delivery system that permits the storage of a unit dose of potentially reactive dental material that can be dispensed precisely with a metal cannula.

SUMMARY OF THE INVENTION

The present invention provides a delivery system for dispensing a dental material precisely using a metal cannula that is prevented from reacting with the dental material. A material capsule, containing a dental material that may react with metal after prolonged contact, has a sealed delivery tip connector end. Upon unsealing the delivery tip connector end, a delivery tip having a metal cannula is securely attached thereto. The material capsule is placed in a syringe for dispensing the dental material through the metal cannula without prolonged contact. The delivery tip may be attached to the material capsule by a snap-fit or threaded connection.

In another embodiment the material capsule has a material bore with a narrowing material bore transition portion and a material delivery orifice. The material capsule also has a widening external material capsule transition ending in an external material capsule opening surface having internal threads for receiving an externally treaded delivery tip having a metal cannula.

It is an object of the present invention to prevent a dental material from reacting with the material of the delivery system.

It is a more specific object of the present invention to prevent a dental material from being in prolonged contact or close proximity with a metal cannula so as to prevent a reaction therewith.

It is yet another object of the present invention to make dentistry easier.

It is another object of the present invention to provide a material capsule that can be easily secured to a delivery tip having a cannula.

It is an advantage of the present invention that a dental material is stored in a unit dose container for prolonged periods without reacting with the capsule or delivery tip.

It is another advantage of the present invention that the dental material is prevented from contacting or being in close proximity with a metal cannula preventing a reaction or contamination of the dental material.

It is yet another advantage of the present invention that the material capsule can be easily held for attaching the delivery tip thereto.

It is a feature of the present invention that a metal cannula is separated from contact with the dental material prior to dispensing the dental material.

It is another feature of the present invention in one embodiment that the material capsule has a snap-off seal adjacent a delivery tip connector end.

It is yet another feature of the present invention that various means are provided for securely holding a delivery tip on to a material capsule.

It is another feature of the present invention that grips are formed on the external material capsule surface adjacent an opening.

It is another feature of the present invention that a radially increasing external transition portion extends between the end of a material bore and an external delivery tip surface and a radially decreasing material bore transition extends between the end of the material bore to a material bore orifice.

These and other objects, advantages, and features will become more readily apparent in view of the following more detailed description.

DETAILED DESCRIPTION OF THE PREFERRED EMBODIMENTS

Figure 1:
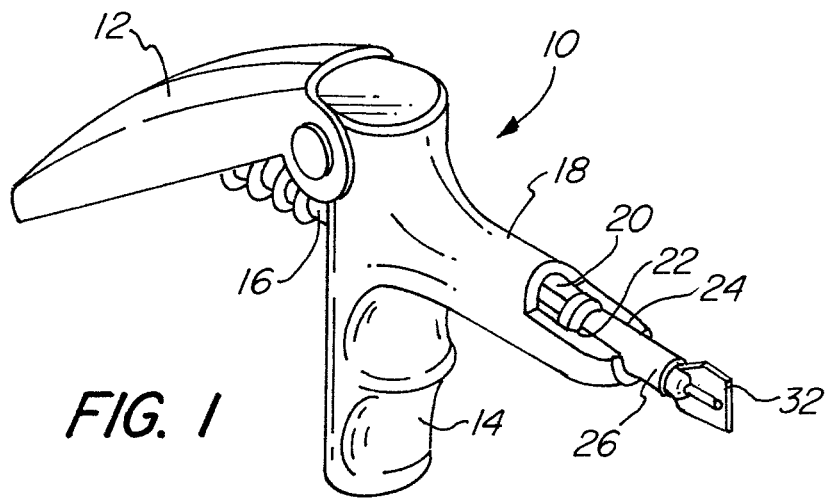
FIG. 1 is a perspective view of the delivery system of the present invention without the attachment of a delivery tip.

FIG. 1 is a perspective view illustrating the delivery system and capsule of the present invention. A syringe 10 has a lever 12 and a piston 16 reciprocally placed within a barrel 18. The lever 12 causes the syringe 10 to have a mechanical advantage permitting the dispensing of viscous dental materials. A breach 20 formed in the barrel 18 has formed therein a shoulder 22 and sidewalls 24. The sidewalls 24 may be flexible, providing a snap-fit around the material capsule 26. The material capsule 26 is illustrated with a breakaway tab 32 thereon.

The syringe 10 may be similar to the syringe disclosed in U.S. Pat. No. 5,489,207, which is herein incorporated by reference.

Figure 2:
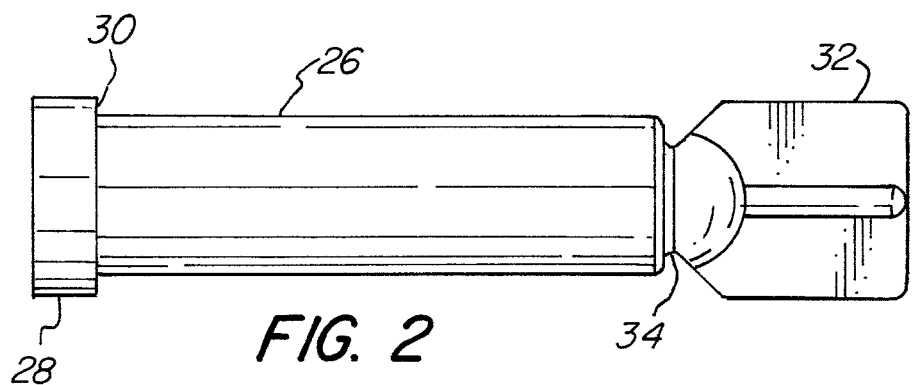
FIG. 2 is a side elevational view of an embodiment of the present invention without the attachment of a delivery tip.

FIG. 2 is a side elevational view more clearly illustrating the features of the material capsule 26. The material capsule 26 has an external flange 28. An external shoulder 30 is formed adjacent flange 28. A notch or web 34 is formed between the breakaway tab 32 and the material capsule 26. The material capsule and breakaway tab 32 is preferably made of plastic.

Figure 3:
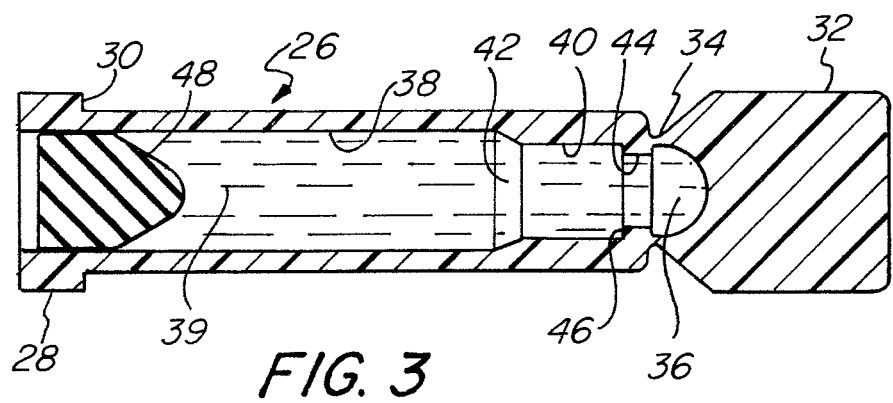
FIG. 3 is a cross-section of the embodiment illustrated in FIG. 2.

FIG. 3 more clearly illustrates the internal structure of the material capsule 26. The material capsule 26 is sealed at one end by a plug or piston 48. The plug or piston 48 may be frictionally fit within the material bore 38 or it may be sonically welded thereto so that it may be easily broken away when advanced. That is the piston 48 is retained in position yet may be broken free for dispensing the reactive dental material when desired.

A dental material 39 is contained within the material capsule 26. An internal angled transition 42 reduces the diameter to a delivery bore 40 adjacent the delivery end portion of the material capsule 26. The delivery end portion has an internal flange 44 that forms an internal shoulder 46. Space 36 permits the web 34 to be formed so that the tab 32 may be broken away from the material capsule 26 forming an opening and exposing the material 39 contained therein.

The dental material may contain a chemical, such as aluminum chloride, which is reactive or caustic to metal. The dental material may be any dental material that may react with the dispensing or delivery tip cannula material. Other caustic materials that may be used include aluminum potassium sulfate, aluminum sulfate, ferric sulfate, aluminum ammonium sulfate or alum, ferric chloride, sodium chloride, zinc chloride, and the like. Preferably, the dental material is a retraction material used to retract gingival tissue from around a tooth. The retraction material may be a clay based retraction material. For example, the dental material my contain white clay or kaolin and aluminum chloride.

Figure 4:
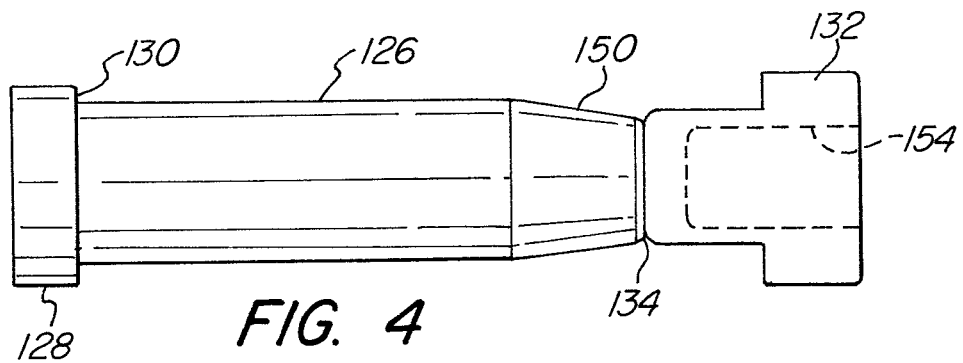
FIG. 4 is a side elevational view of another embodiment of the present invention without the attachment of a delivery tip.
Figure 5:
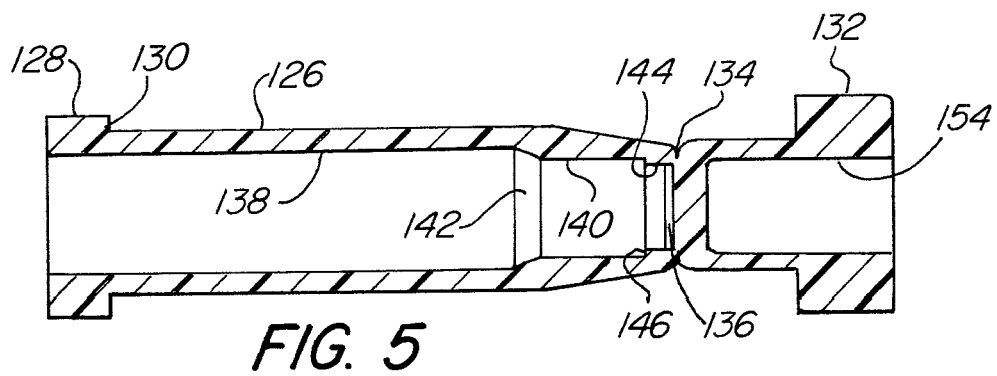
FIG. 5 is a cross-section of the embodiment illustrated in FIG. 4.

FIGS. 4 and 5 illustrate a slightly modified version of a material capsule 126. The material capsule 126 has an external flange 128 that forms an external shoulder 130. A breakaway tab 132 is attached to the material capsule 126 by web 134. The material bore 138 has an internal angled transition 142 entering the delivery bore 140. A space 136 is formed adjacent the delivery end and permits the web 134 to be formed. An internal flange 144 forms internal shoulder 146.

Figure 6:
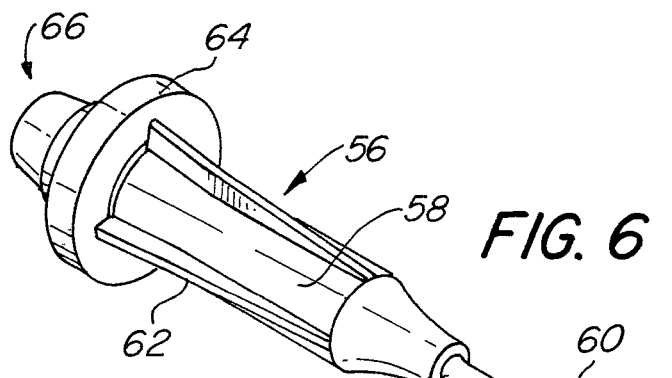
FIG. 6 is a perspective view of an embodiment of delivery tip.
Figure 7:
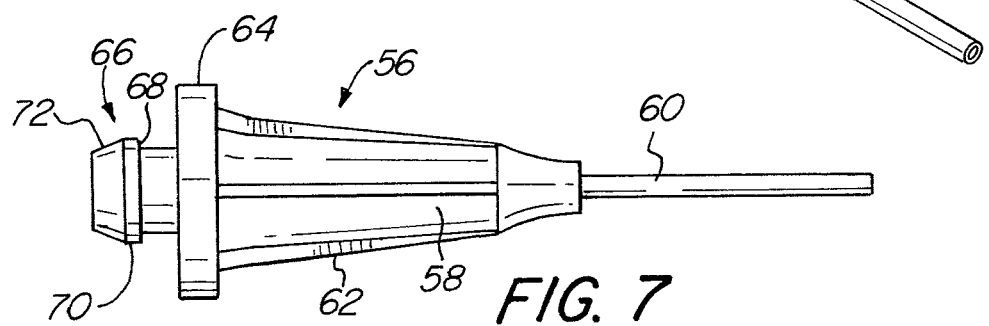
FIG. 7 is a side elevational view of the delivery tip illustrated in FIG. 6.

FIGS. 6 and 7 illustrate a delivery tip 56. The delivery tip 56 comprises a body portion 58 having ribs 62 thereon. The body portion 58 and ribs 62 are preferably made of plastic. A metal cannula 60 is formed on one end. A delivery tip connector end 66 is formed on the other end. Flange 64 is placed adjacent the delivery tip connector end 66. The delivery tip connector end 66 has a shoulder 68, a flat portion 70 and an angled portion 72. Upon removal of the breakaway tab 132, illustrated in FIG. 5, the delivery tip 56 may be placed on the material capsule 126 by inserting the delivery tip connector end 66 into the opening formed by the internal flange 144. The shoulder 168 of the delivery tip connector end 66 mates with the internal shoulder 146 of the material capsule 126. Accordingly the delivery tip 56 is securely connected to the material capsule 126 when the material contained therein is dispensed. This separation of the delivery tip 56 from the material capsule 26 prevents the material contained within the material capsule 126 from contacting the metal cannula 60 for prolonged periods. Therefore the material only contacts the metal cannula 60 for a relatively short period of time, substantially preventing any contamination or corrosive effect.

Figure 8:
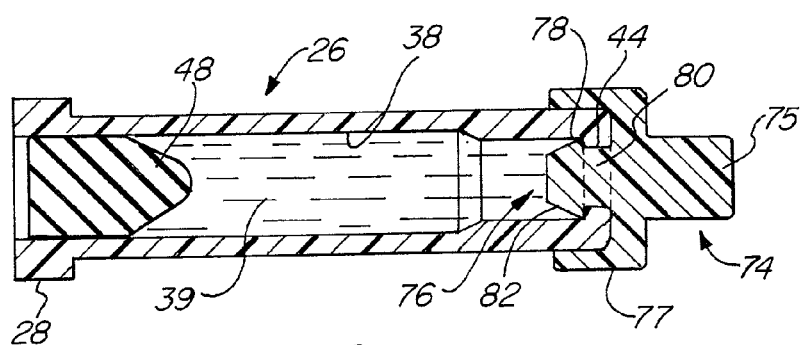
FIG. 8 is a longitudinal cross section of an embodiment of the present invention using a snap-on cap.

FIG. 8 illustrates an embodiment of the present invention utilizing a snap-on cap 74. The snap-on cap 74 may be used in place of the breakaway tab or in combination therewith when the breakaway tab has been removed and the material capsule 26 is desired to be sealed again. The snap-on cap 74 has a handle 75 and a cap connector end 76. A cap cover portion 77 helps retain the snap-on cap 74 in position and to seal the material capsule 26. The angled portion 82 and the combination of the shoulder 78 and internal flange 44 and flat portion 80 assure that the snap-on cap 74 is securely held in position and seals the opening of the material capsule 26.

Figure 9:
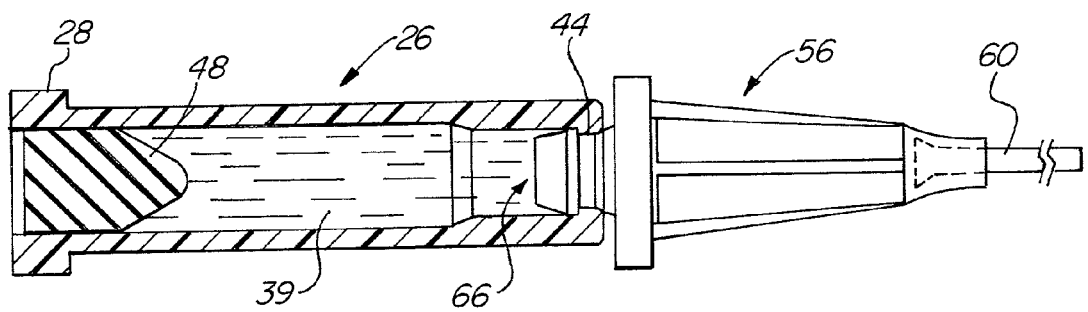
FIG. 9 is a side elevational view in partial cross section illustrating the material capsule and attached delivery tip.

FIG. 9 illustrates the delivery tip 56, with the metal cannula 60, attached to the material capsule 26. The delivery tip connector end 66 of the delivery tip 56 securely mates with the internal flange 44 formed on the material capsule 26. Upon advancing piston 48 the dental material 39 is extruded or forced out of the delivery tip 56 through the metal cannula 60. The ability to unseal the material capsule 26 and to place the delivery tip 56 thereon just prior to the use of the dental material 39 prevents the prolonged contact of the dental material 39 with the metal cannula 60. This prevents the possibility of corrosion or a reaction occurring due to prolonged contact of the dental material with the metal cannula 60. This results in greatly improved performance of some reactive dental materials.

Figure 10:
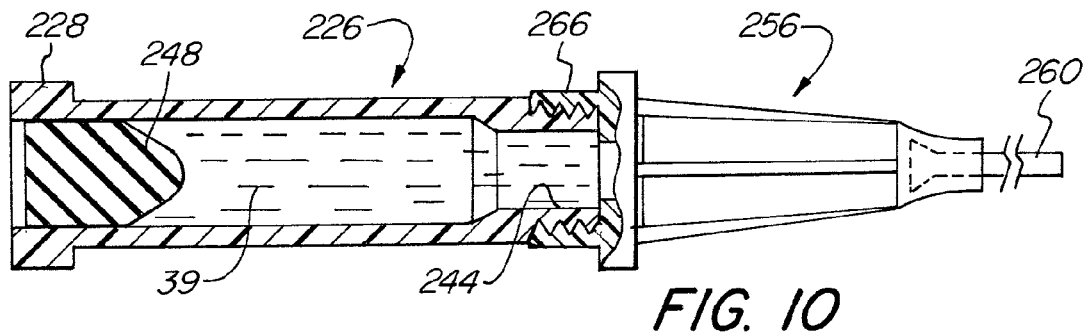
FIG. 10 is a slide elevational view in partial cross section illustrating the material capsule having an externally threaded delivery end portion and attached delivery tip.

FIG. 10 illustrates another embodiment of the present invention that may be utilized when thick or viscous dental materials are used therewith so as to prevent the delivery tip from separating from the material capsule 226. In this embodiment the material capsule 226 having flange 228 and plug 248 has an externally screw threaded end 244 that mates with the internally screw threaded tip connector end 266 of the delivery tip 256. Accordingly a relatively viscous dental material 39 when forced through the cannula 260 will not cause the screw threaded delivery tip 256 to separate from the screw threaded material capsule 226.

Figure 11:
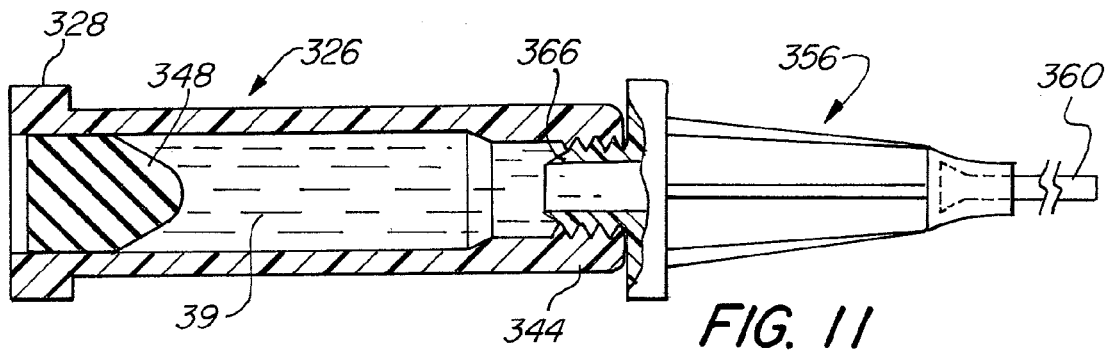
FIG. 11 is a side elevational view in partial cross section illustrating the material capsule having an internally threaded delivery end portion and attached delivery tip.

FIG. 11 illustrates another embodiment having an internally threaded end 344. The internally threaded end 344 is formed within the open end of the material capsule 326 having external flange 328 and plug or piston 348. The delivery tip 356 has an externally threaded tip connector end 366 that mates with the internally threaded end 344 providing a secure connection. Accordingly, viscous dental material 39 extruded through the metal cannula 360 by advancing plug or piston 348 will not result in separation of the delivery tip 356 and the material capsule 326.

Figure 12:
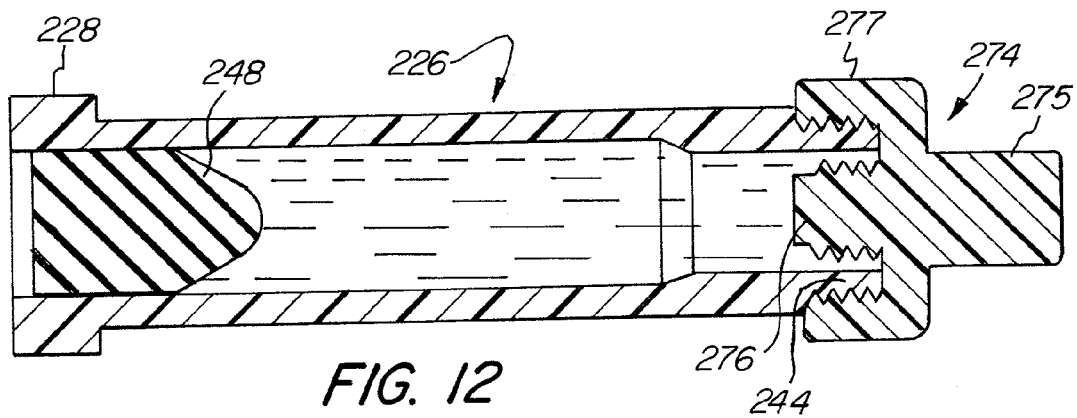
FIG. 12 is a longitudinal cross section of an embodiment of the present invention having a material capsule and attached universal threaded cap.

FIG. 12 illustrates an embodiment using a universal threaded cap 274. The universal cap 274 has a handle 275 and an internally threaded cap connector 276 and an externally threaded cap cover 277. The universal threaded cap 274 may be used on either the externally threaded end 244 of material capsule 226 or the internally threaded end 344 formed on the material capsule 326. Universal threaded cap 274 may be used in place of or in combination with a breakaway tab.

Figure 13:
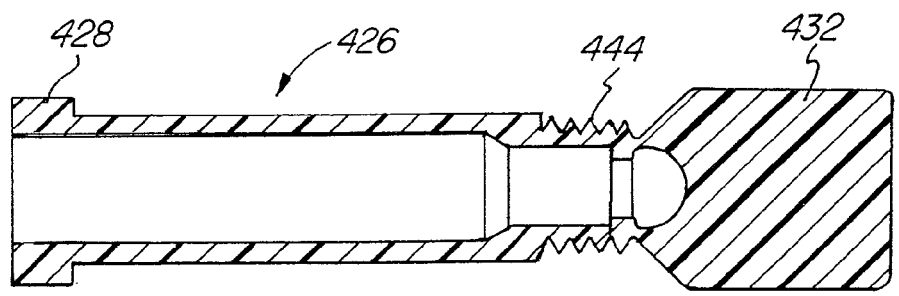
FIG. 13 is a longitudinal cross section of another embodiment of the present invention having a breakaway tab and externally threaded delivery end portion.

FIG. 13 illustrates another embodiment wherein the material capsule 426 has an external flange 428 on one end and an externally threaded tip end 444 on the other end and in combination with a breakaway tab 432. In this embodiment the breakaway tab 432 may be removed forming an opening and an internally threaded delivery tip 256 placed thereon, as illustrated in FIG. 10.

Figure 14:
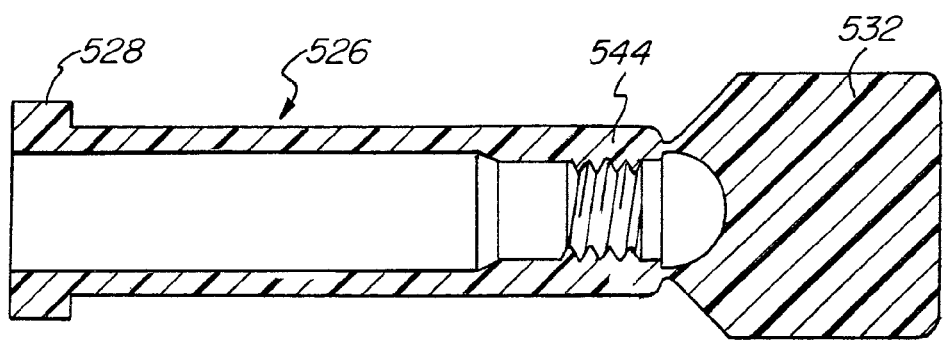
FIG. 14 is a longitudinal cross section of another embodiment of the present invention having a breakaway tap and an internally threaded delivery end portion.

FIG. 14 illustrates another embodiment where the material capsule 526 has an external flange 528 on one end and an internally threaded tip end 544 on the other end. In this embodiment a breakaway tab 532 may be removed forming an opening and an externally threaded delivery tip 356, as illustrated in FIG. 11, may be threaded onto the internally threaded tip end 544.

Figure 15:
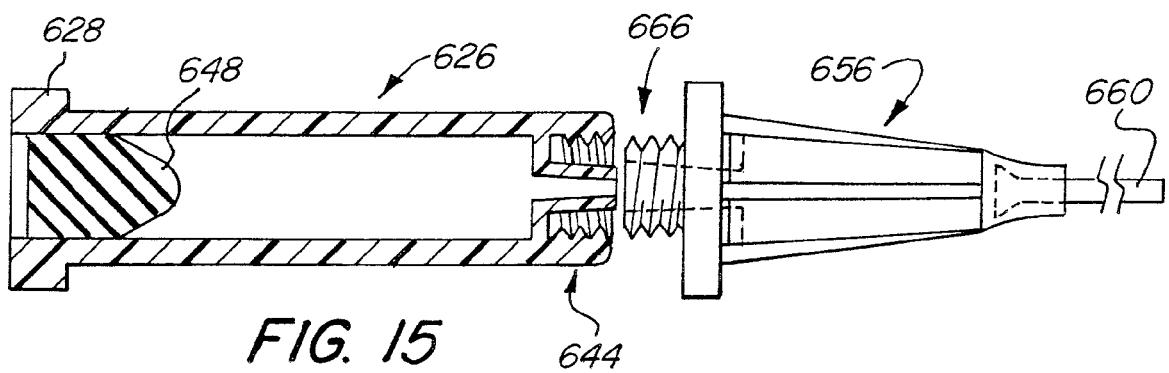
FIG. 15 is a side elevational view in partial cross section illustrating the material capsule and attached delivery tip having a Luer lock type connection.

FIG. 15 illustrates another embodiment having a Luer lock type connector. A Lure type connector has male and female slightly tapered tubes that interlock providing a secure fitting attachment. FIG. 15 illustrates a material capsule 626 having an external flange 628 and a piston 648 in one end and a male Luer lock type connector 644 on the other. Delivery tip 656 has a metal cannula 660 on one end and a female Luer lock type connector 660 on the other end.

Figure 16:
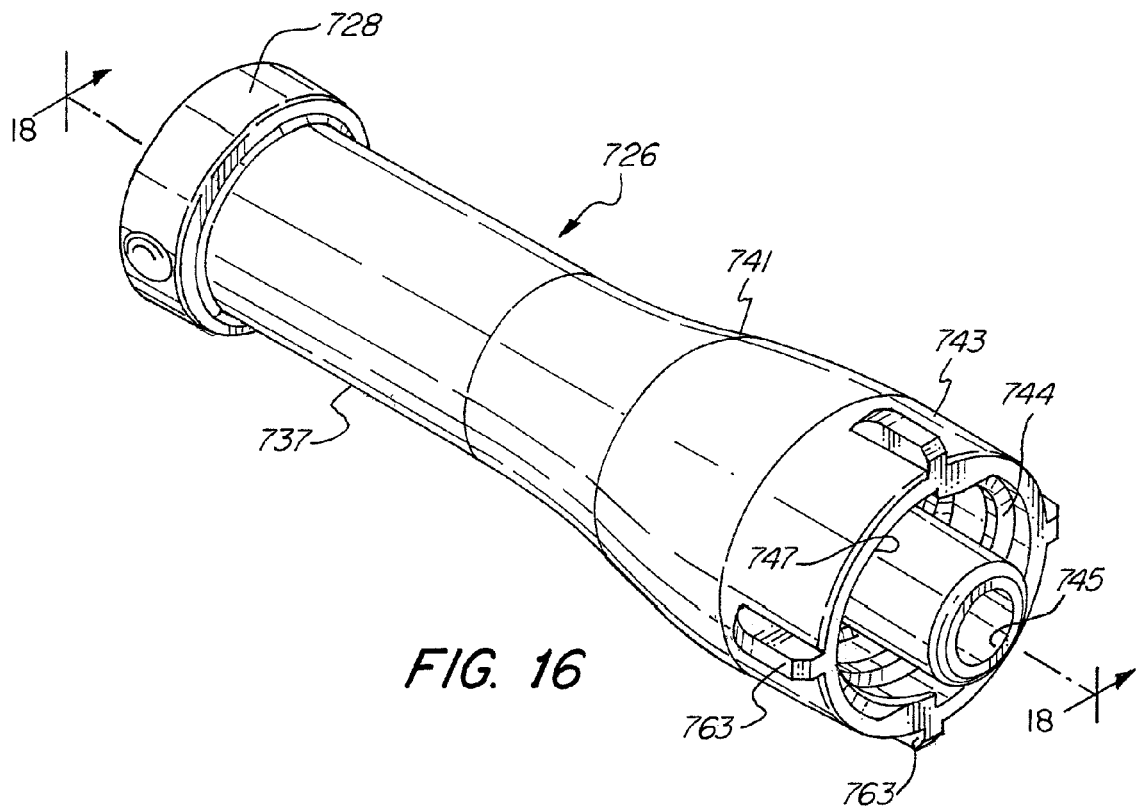
FIG. 16 is a perspective view of another embodiment of the invention having a radially increasing external material capsule transition and a Luer lock type connection for receiving a delivery tip.
Figure 17:
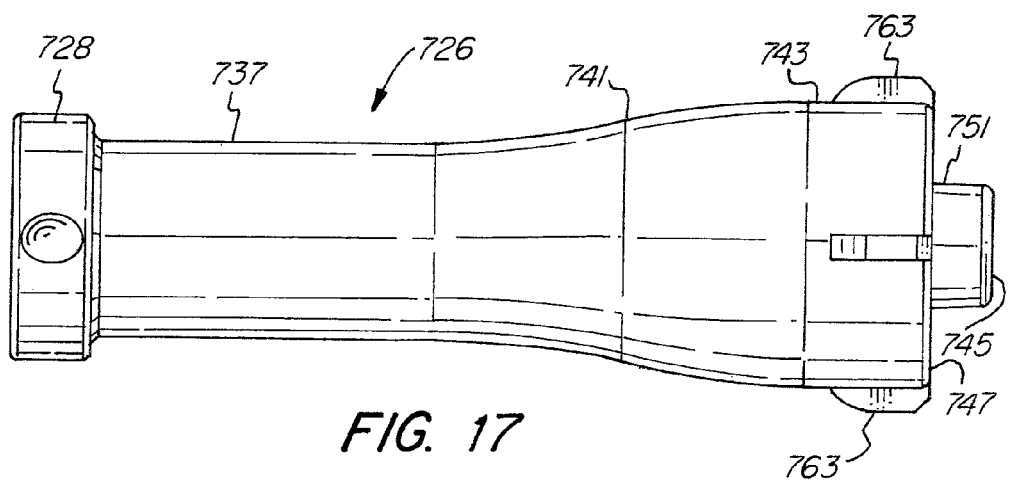
FIG. 17 is a side elevational view of the embodiment illustrated in FIG. 16.
Figure 18:
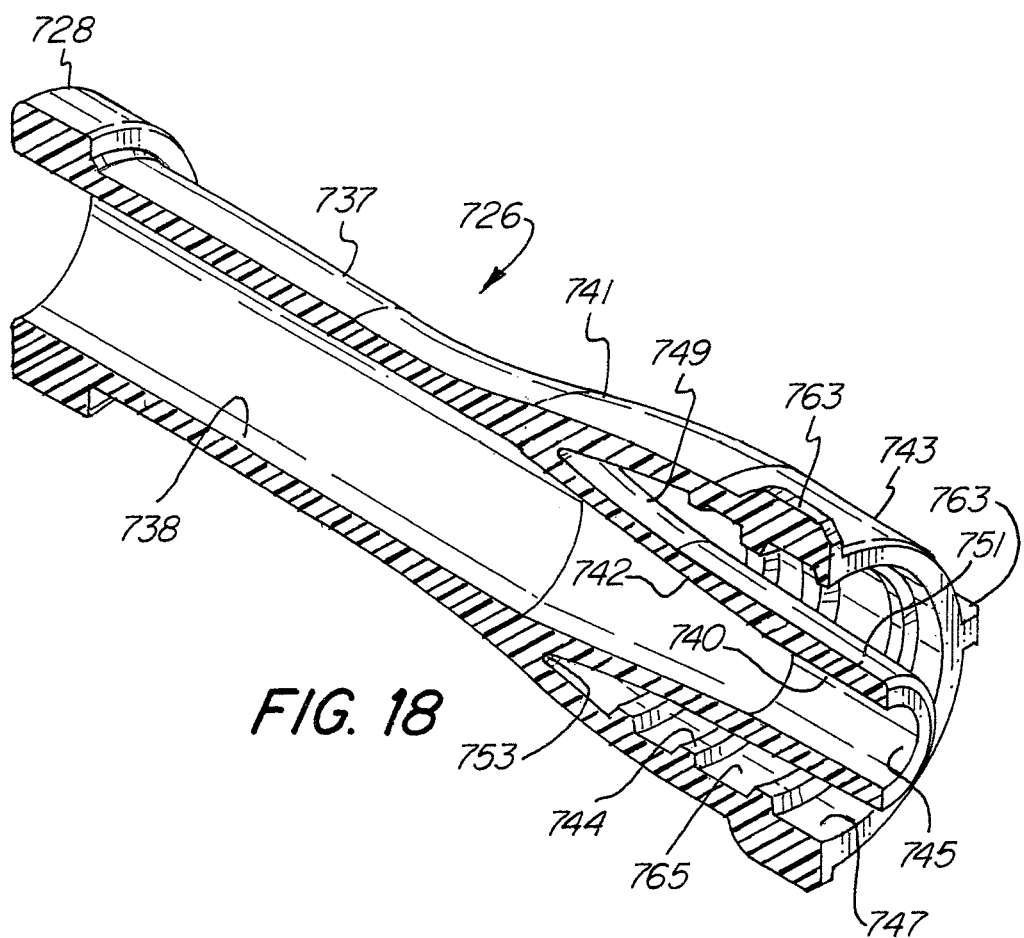
FIG. 18 is a cross section perspective view taken along line 18-18 in FIG. 16.

FIGS. 16-18 illustrate another embodiment of the present invention that is similar to the embodiment illustrated in FIG. 15. The material capsule 726 has an external flange 728 and an external material capsule surface 737. Adjacent the external material capsule surface 737 is a radially increasing external material capsule transition 741 extending to the external material capsule opening surface 743. On the external material capsule opening surface 743 are placed grips 763. Placed on the interior surface of the external material capsule opening surface 743 are internal threads 744. The internal threads 744 are adapted to receive male threads on a delivery tip, such as that the delivery tip 656 illustrated in FIG. 15. Extending from the material capsule opening 747 is a material delivery orifice 745. As illustrated in FIG. 17, this material delivery orifice 745 has an external delivery tip surface 751 that extends beyond the material capsule opening 747.

FIG. 18 is a cross section perspective view better illustrating the interior of the material capsule 726. In this view the transition of the constant diameter material bore 738 to the radially decreasing material bore transition inner surface 742 is clearly illustrated. The material capsule 726 has an entrance end for receiving a material and a plug or piston adjacent external flange 728, as illustrated in the prior figures, and an opposing dispensing end adjacent the radially decreasing material bore transition inner surface 742. The radially decreasing material bore transition inner surface 742 extends to the material delivery bore 740 which opens to the material delivery orifice 745. In this embodiment of the material capsule 726 there is a smooth transition from the constant diameter material bore 738 through the radially decreasing material bore transition inner surface 742 to the material delivery orifice 745. The sidewall of the material capsule 726 divides approximately adjacent the end of the material bore 738 and beginning of the radially increasing external material capsule transition 741 at a bisected sidewall apex 753. Accordingly, the radially decreasing material bore transition external surface 749 diverges with the radially increasing external material capsule transition 741 forming an increasing radial dimension gap there between forming the material capsule opening 747 opposite the bisected sidewall apex. Internal threads 744 are formed on an inner material capsule opening surface 765, and are adapted to mate with a delivery tip having a female Lure lock type end.

This embodiment improves the dispensing of viscous dental materials contained within the material bore 738. For example, the dental material may be a clay based gingival retraction paste that contains aluminum chloride and kaolin clay. Preferably the retraction paste contains fifteen percent of aluminum chloride. The retraction paste is placed in the material bore 738 and sealed with a plug adjacent the external flange 728, as illustrated in FIG. 15, with the material delivery orifice 745 sealed with a removable cap as illustrated in FIGS. 8 and 12. The material capsule 726 may then be placed in a sealed foil package separately from the delivery tip having a metal cannula. This prevents the potentially caustic aluminum chloride from reacting over a period of time with the metal cannula.

The material in the material capsule 736 is easily dispensed by placing the material capsule 736 into a syringe 10 as illustrated in FIG. 1. A plug or piston, as illustrated in the prior figures, is placed in the material bore 738 to extrude a viscous dental material out of the material delivery orifice 745 and through an attached delivery tip.

Figure 19:
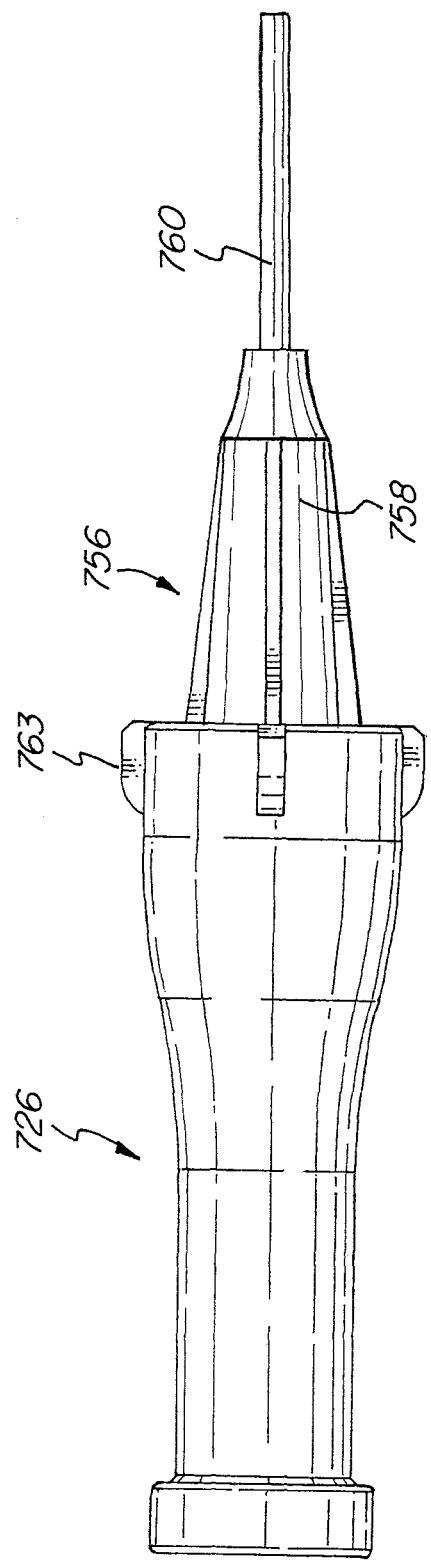
FIG. 19 is a side elevational view of the embodiment illustrated in FIG. 16 having a delivery tip attached.

FIG. 19 is a side elevational view illustrating a delivery material capsule system with the material capsule 736 having a delivery tip 756 attached. The delivery tip 756 has a body 758 and a metal cannula 760. The metal cannula 760 may be ductile or easily bent. The delivery tip 756 may be attached to the material capsule 726 by any type of attachment, but is preferably threaded onto the material capsule 726. The grips 763 greatly facilitate the threading of the delivery tip 756 onto the material capsule 726.

Accordingly, the various embodiments of the present invention all provide for a potentially caustic or reactive dental material to be separated in a sealed material capsule, preventing prolonged contact with a metal cannula used for precisely placing the dental material in a patient's mouth. It is desirable that the potentially caustic or reactive dental material is not only kept from direct contact with the metal cannula, but that the potentially caustic or reactive dental material is kept out of proximity with the metal cannula and is preferably not sealed in the same package. For example, the material capsule containing the dental material may be packaged in a sealed pouch separately from the delivery tip with the metal cannula. Additionally, the embodiment having the piston or plug sonically welded to the material capsule may be advantageous to prevent corrosive gases form the potentially caustic or reactive dental material from escaping. The metal cannula should be kept from prolonged contact or proximity with any possible volatile gaseous components of the potentially caustic or reactive dental material. The present invention therefore greatly facilitates a unit dose material dispensing system that can be used with reactive or caustic dental materials. The present invention therefore provides for improved results and makes dentistry easier.

While the present invention has been described with respect to several embodiments, it should readily be appreciated that various modifications may be made without departing from the spirit and scope of this invention.

What is claimed is:

1. A delivery system for dispensing potentially reactive or caustic viscous dental material through a metal cannula comprising:
    a material capsule having a material bore with a constant diameter and an external material capsule surface, the material bore having an entrance end and a dispensing end;
    an external flange formed on said material capsule adjacent the entrance end;
    a bisected sidewall apex formed in said material capsule adjacent the dispensing end of the material bore;
    a radially decreasing transition bore having a continuous smooth transition inner surface, wherein the continuous smooth transition inner surface forms a continuous smoothly decreasing diameter bore adjacent the dispensing end of the material bore and extending from said bisected sidewall apex, said radially decreasing transition bore having a continuous smooth transition inner surface ending in a material delivery bore with an orifice;
    a radially increasing continuous smooth external material capsule transition surface adjacent the dispensing end of the material bore and extending from said bisected sidewall apex, said radially increasing continuous smooth external material capsule transition surface ending in an external material capsule opening surface with an opening, wherein a gap having an increasing radial dimension progressing from said bisected sidewall apex to the opening is formed between said radially decreasing transition bore having a continuous smooth transition inner surface and said radially increasing continuous smooth external material capsule transition surface;
    a plurality of radially extending grips having a longitudinal extent in an axial direction placed on the external material capsule opening surface adjacent the opening;
    internal threads formed within the gap on an internal material capsule opening surface adjacent the opening; and
    a delivery tip having a metal cannula attaching to said internal threads,
    whereby the caustic or reactive dental material is intended to be contained separately in said material capsule and prevented from contacting or residing in proximity to the metal cannula prior to being dispensed.

2. A delivery system for dispensing potentially reactive or caustic viscous dental material through a metal cannula as in claim 1 further comprising:
    a retraction dental material placed in said material capsule.

3. A delivery system for dispensing potentially reactive or caustic viscous dental material through a metal cannula as in claim 2 wherein:
    said retraction dental material comprises aluminum chloride and kaolin clay.

4. A delivery system for dispensing potentially reactive or caustic viscous dental material through a metal cannula comprising:
    a material capsule having a material bore with a constant diameter and an external material capsule surface, the material bore having an entrance end and a dispensing end;
    an external flange formed on said material capsule adjacent the entrance end;
    a bisected sidewall apex formed in said material capsule adjacent the dispensing end of the material bore;
    a radially decreasing transition bore having a continuous smooth transition inner surface, wherein the continuous smooth transition inner surface forms a continuous smoothly decreasing diameter bore adjacent the dispensing end of the material bore and extending from said bisected sidewall apex, said radially decreasing transition bore having a continuous smooth transition inner surface ending in a material delivery bore with an orifice;
    a radially increasing continuous smooth external material capsule transition surface adjacent the dispensing end of the material bore and extending from said bisected sidewall apex, said radially increasing continuous smooth external material capsule transition surface ending in an external material capsule opening surface with an opening, wherein a gap having an increasing radial dimension progressing from said bisected sidewall apex to the opening is formed between said radially decreasing transition bore having a continuous smooth transition inner surface and said radially increasing continuous smooth external material capsule transition surface;
    a plurality of radially extending grips having a longitudinal extent in an axial direction placed on the external material capsule opening surface adjacent the opening;

internal threads formed within the gap on an internal material capsule opening surface adjacent the opening;

a delivery tip having a metal cannula adapted to be attached to said internal threads;

a dental material placed within the material bore of said material capsule, said dental material being caustic or reactive to the metal cannula of said delivery tip;

means, associated with said material capsule, for keeping said material capsule and said dental material out of proximity and prolonged contact with the metal cannula of said delivery tip, whereby the caustic or reactive dental material is intended to be contained separately in said material capsule and prevented from contacting or residing in proximity to the metal cannula prior to being dispensed.

5. A delivery system for dispensing potentially reactive or caustic viscous dental material through a metal cannula as in claim 4 wherein:

said means for keeping said material capsule and dental material out of proximity and prolonged contact with the metal cannula of said delivery tip comprises a sealed pouch.

6. A delivery system for dispensing potentially reactive or caustic viscous dental material through a metal cannula as in claim 4 wherein:

said dental material comprises aluminum chloride and kaolin clay.

\* \* \* \* \*